United States Patent [19]

Chilton et al.

[11] Patent Number: 4,706,683

[45] Date of Patent: Nov. 17, 1987

[54] METHOD AND APPARATUS FOR BOLUS DELIVERY OF GASES AND AEROSOLS AND INSUFFLATIONS

[75] Inventors: Henry Chilton, Louisville, N.C.; Lester Dickson, Budd Lake, N.J.

[73] Assignee: Bowman Gray School of Medicine, Wake Forest University, Winston-Salem, N.C.

[21] Appl. No.: 811,814

[22] Filed: Dec. 20, 1985

[51] Int. Cl.⁴ .............................................. A61B 6/00
[52] U.S. Cl. .............................. 128/654; 128/201.26; 128/203.12; 128/203.29; 128/206.29; 128/205.25
[58] Field of Search ........... 128/1.1, 654, 730, 203.12, 128/203.29, 203.21, 201.26, 205.25, 206.28, 206.29, 207.14; 604/24, 26

[56] References Cited

U.S. PATENT DOCUMENTS 3,666,955  5/1972  Suprenant et al. .
3,881,463  5/1975  LeMon .
3,957,033  5/1975  Winchell et al. .
4,192,438  3/1980  Foster et al. .
4,202,345  5/1980  Farella et al. .
4,513,741  4/1985  Demi .............................. 128/206.29

OTHER PUBLICATIONS

Mallinckrodt, "The Xenomatic System".
"Xenon Xe 133 Gas Calidonse Dispensing System".
"Injection Port Air-Cushioned Face Mask".
Atomic Products Corporation "Atomlab News".

Primary Examiner—William E. Kamm
Assistant Examiner—Randy Citrin
Attorney, Agent, or Firm—Oblon, Fisher, Spivak, McClelland & Maier

[57] ABSTRACT

A method and apparatus for the bolus administration of a gas such as a radioactive gas includes a face mask defining a closed space into which a straw-like administration tube extends sufficiently to permit a patient wearing the face mask to suck on the tube. The radioactive gas is introduced through the administration tube and exhaled into the face mask.

27 Claims, 6 Drawing Figures

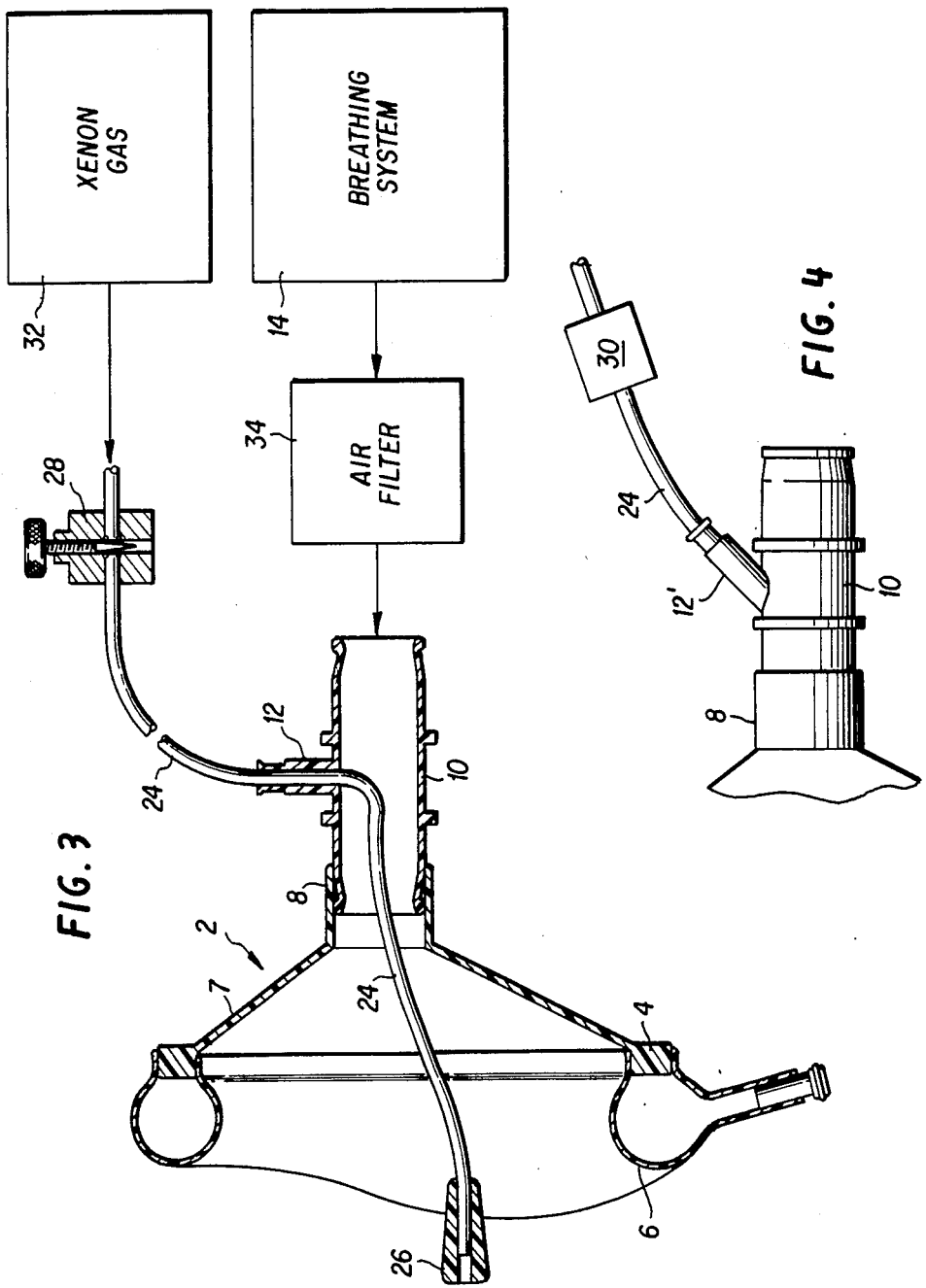

METHOD AND APPARATUS FOR BOLUS DELIVERY OF GASES AND AEROSOLS AND INSUFFLATIONS

BACKGROUND OF THE INVENTION

The present invention relates to a method for the administration via bolus type delivery of medicaments employed for either diagnostic studies—such as radioactive gases, aerosols or insufflations for studying pulmonary ventilation function—or for therapeutic applications. The latter application is for agents whose administration via inhalation is beneficial to the drug's absorption or desired drug-effects. More specifically, the present invention relates to the administering of gases such as radioactive gases, usually radioactive Xenon, to a patient during studies of lung functioning.

Diagnostic techniques are known in which a radioactive gas, typically Xenon gas, is administered to a patient. After the patient has inhaled the gas, a scintillation imaging device is employed to obtain images of the lungs by detecting the presence of radioactivity on a positional basis. Additional diagnostic information can be obtained by observing the distribution of the radioactive gas in the lungs over time, again using the scintillation detector to obtain images.

Maximum diagnostic effectiveness of this technique is achieved when radioactive gas enters the lungs of the patient in the desired amount as a bolus—that is, as a dose of the radioactive gas administered at a high concentration in a single inhalation. For this purpose, it has been known to administer the radioactive gas through a mouthpiece connected via appropriate tubing to a closed breathing system including a source of Xenon gas.

The term "Xenon gas" as used throughout the present application refers not only to Xenon gas but to other radioactive gases and radioactive pharmaceuticals which can or may be used in lung studies, including Krypton Kr81m, and gases, aerosols and insufflations of other radionuclides.

An example of such a known system is shown in U.S. Pat. No. 3,957,033 to Winchell et al, the subject matter of which is hereby incorporated by reference. In Winchell et al, a mouthpiece is connected to a sealed gas retaining volume. As a patient breathes via the mouthpiece 21, a valve plug can be used to release Xenon gas from a Xenon gas enclosing capsule so that the air from the gas retaining volume and the Xenon gas are inhaled. The Xenon gas is subsequently exhaled back into the mouthpiece.

This technique has several shortcomings. First, a nose clip is required to prevent the patient from either breathing room air or exhaling radioactive gas into the immediate environment. Such a nose clip can be uncomfortable and prevent the patient from breathing normally. Additionally, it may be resisted by the patient. Moreover, since patients requiring such lung studies are often quite ill and may have difficulty breathing, it may be particularly difficult for the patient to maintain a tight seal with his lips on the mouthpiece during exhaling so leakage of the radioactive gas from the patient's mouth may occur. For example, the patient may cough upon inhaling the Xenon gases in which case the entire dose will be discharged to the ambient atmosphere. This can pose health hazards for personnel administering the procedure, particularly after repeated situations where accidental environmental release occurs.

In an effort to avoid these problems, it has been known to administer Xenon gas by use of a breathing or face mask which fits over a patient's mouth and nose and to connect the breathing mask to a shielded and sealed breathing system having a spirometer type volume for containing the Xenon during the study as well as a trap for the Xenon gas. This is shown in U.S. Pat. No. 4,202,345 to Farella et al, the subject matter of which is hereby incorporated by reference. There, the face mask is connected via a plurality of tubes to the breathing system and the Xenon gas is injected into one of the tubes leading to the face mask. During the lung functioning study of Farella et al, a patient initially breathes atmospheric air. The system is subsequently sealed and the patient inhales purified air from a bag within the system while at the same time the Xenon gas is injected into the air of the face mask via a separate conduit. Subsequently, the patient exhales the air including the Xenon gas which is returned to the bag within the breathing system.

However, the proper functioning of this procedure requires that the patient inhale through the face mask at precisely the same time that the Xenon gas is injected, and that all of the Xenon gas is inhaled as a bolus in a single inhalation. If the patient has difficulty in breathing or does not inhale at precisely the proper moment, part or all of the Xenon gas will become diffused into the air of the general system and may not reach the patient's lungs as the desired bolus type volume.

FIG. 1 shows a curve illustrating the Xenon gas concentration in the lungs of a patient during a lung functioning study. An ideal gas concentration curve is shown by a solid line. The Xenon gas should be administered in a bolus so that there is an immediate almost vertical rise in gas concentration to a peak value which gives high resolution images from the scintillation imaging device. Over time, and as the patient breathes, the Xenon gas concentration reaches an equilibrium value and eventually washes out to a residual concentration as the closed system is opened for air intake only and the expired Xenon is trapped and contained within the breathing system. The amount of Xenon administered initially provides beneficial diagnostic information (via the scintillation images) concerning lung ventilation. Bolus type administration of Xenon facilitates the quality of these images. However, if the Xenon gas is not administered in a bolus, as can occur by use of the conventional system such as that of Ferrala et al, the Xenon gas concentration curve can have the shape shown in dashed lines in FIG. 1. This curve lacks the peak of the ideal curve and so provides less complete diagnostic information, particularly during the initial phases of lung imaging when data on air movement into lungs might otherwise be obtained.

SUMMARY OF THE INVENTION

It is an object of the present invention to provide an improved method for the administration of gaseous, aerosol or insufflation type medicaments during diagnostic or therapeutic procedures.

It is a further object of the present invention to provide an improved method for the bolus administration of gaseous, aerosol or insufflation type medicaments during diagnostic or therapeutic procedures.

It is a further object of the present invention to provide an improved method for the administration of a radioactive gas such as Xenon gas to a patient during a lung functioning study.

It is yet a further object of the present invention to provide an apparatus for carrying out the improved method of the present invention.

According to the present invention, a face mask is connected to a respiratory gas volume in a shielded breathing system. An administration means such as a straw-like administration tube connected to a source of a substance which may be Xenon gas extends into a closed space defined in part by the cavity of the face mask to a position such that a patient wearing the face mask can take the open end of the administration tube in his mouth and inhale while sucking on the administration tube. At the onset of a procedure such as a lung functioning study, but which may be another diagnostic or therapeutic procedure, the patient is asked to inhale through or suck on the tube while Xenon is introduced into the tube via an interfacing means. Applicant has discovered that a sucking action is relatively easy for individuals in lung distress and is less likely to cause coughing. Moreover, since the patient is actually sucking on the administration tube when the Xenon gas is administered, there is a much higher likelihood that the full dose of Xenon gas will be delivered as a bolus to the patient's lungs in a single inhalation. Finally, exhaling of the gas can be performed by simply breathing into the face mask, without attempting to exhale all of the gas into the administration tube. The face mask assures that the Xenon gas so exhaled will be maintained within the sealed breathing system for subsequent disposal and trapping.

A differential pressure one-way valve attached to a portion of the administration tube permits the patient to inhale air through the administration tube before the injection of the bolus. The injection of the bolus into the administration tube causes the one-way valve to temporarily close, but subsequent suction by the patient reopens the one-way valve, thereby helping to drive the bolus deep into the patient's airways.

BRIEF DESCRIPTION OF THE PREFERRED EMBODIMENTS

Various other objects, features and attendant advantages of the present invention will be more fully appreciated as the same becomes better understood from the following detailed description when considered in connection with the accompanying drawings in which like reference characters designate like or corresponding parts throughout the several views and wherein:

FIG. 3 is a sectional view similar to FIG. 2, and illustrating the apparatus with the optional air filter;

FIG. 4 is a partial view illustrating a variation of a portion of the invention;

Figure 5:
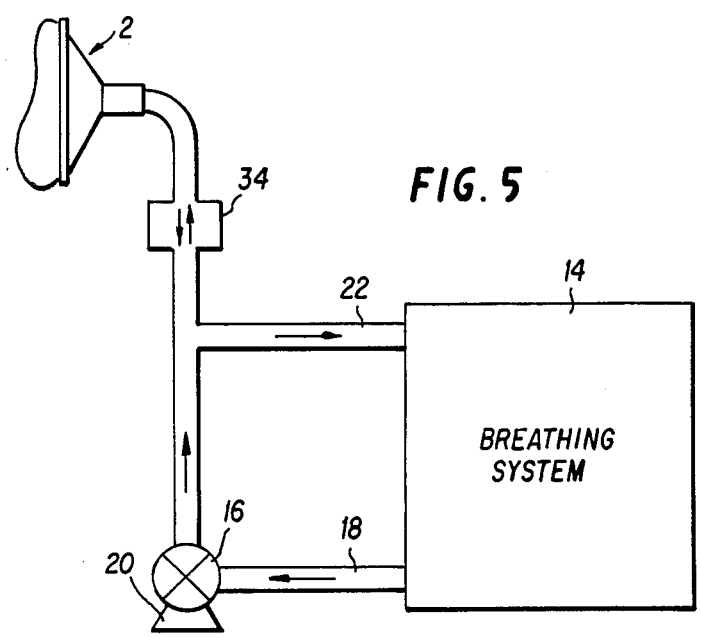
Figure 6:
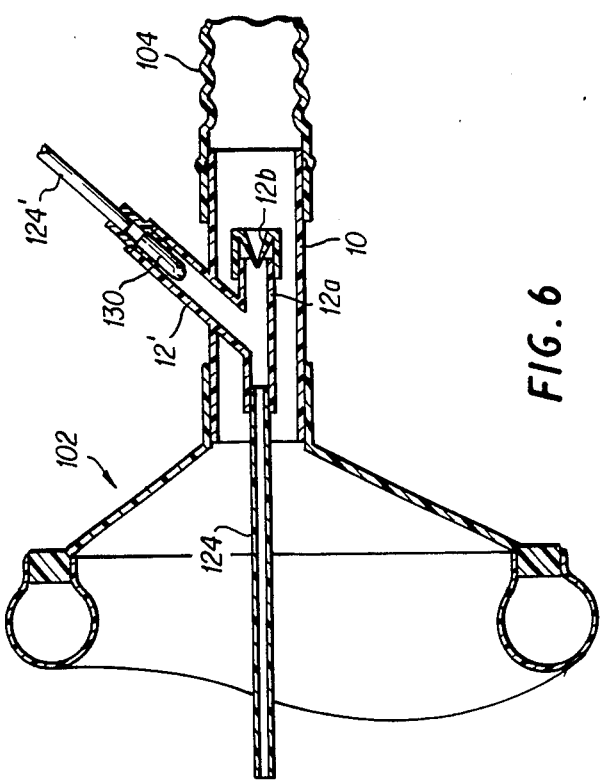

FIG. 5 schematically shows the apparatus of the invention connected to a conventional breathing system; and FIG. 6 is a sectional view of a further embodiment of the invention.

DETAILED DESCRIPTION OF THE PREFERRED EMBODIMENTS

The preferred embodiments of the invention will now be described with reference to the attached figures wherein like reference numerals are used to refer to the same or corresponding parts throughout the several views.

Figure 2:
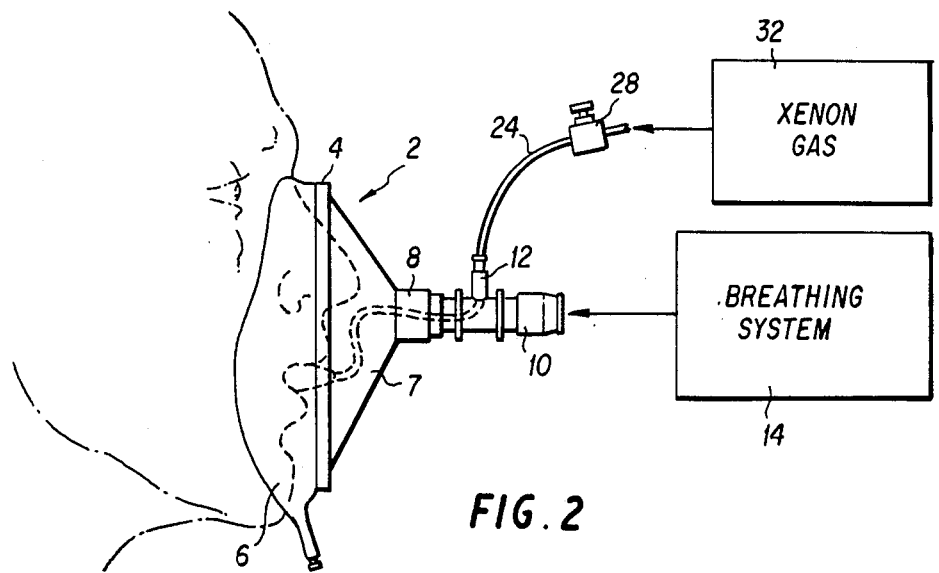
FIG. 2 is a view of a patient wearing the apparatus of the present invention.

As seen in FIGS. 2 and 3, a non-inflatable face mask 2 is positionable so as to fit over a patient's mouth and nose. The face mask is preferably formed of transparent plastic and may be of a conventional design, such as that manufactured by Vital Signs, Inc. of Totowa, N.J. The face mask may include an oval rim for supporting an air filled sealed bladder 6 which forms a seal around the patient's face. The bladder defines the extremities of a face opening for the face mask into which the patient can insert his mouth and nose. A frusto-conical cover 7 defines a cavity and completes the face mask and terminates in a flange 8 for attachment of a breathing tube 10. The breathing tube 10 may be attached to the flange 8 by adhesive, or by a friction fit, so long as the two form an air tight seal.

A sleeve 12 extends from the wall of the tube 10. The sleeve 12 may be attached to the breathing tube 10 by an adhesive, or may be unitarily formed therewith. Preferably, both are formed of rigid transparent plastic. The sleeve 12 can extend at 90° from the longitudinal axis of the breathing tube 10, as shown in FIG. 2, or may be angled away from the face mask, as shown at 12' in FIG. 4.

The distal end of the breathing tube 10 is connected to a shielded breathing system 14 such as that shown in U.S. Pat. No. 4,202,345 or to the Pulmonex Xenon system of the Pulmonex Corporation.

The attachment of the breathing tube 10 to a breathing system is schematically shown in FIG. 5. The breathing system includes a three way valve 16. In a first position, the three way valve opens to permit inhalation of purified air through the conduit 18. In a second position the three way valve permits the introduction of atmospheric air through port 20. In a third position the three way valve is closed and requires exhaled air to enter the breathing system through the conduit 22.

A flexible straw-like Xenon gas administration tube 24 extends through the sleeve 12 and into the tube 10. The portion of the administration tube 24 extending outward from the sleeve 12 may be formed uniformly with the sleeve 12. From there, the Xenon gas administration tube 24 enters the face mask and terminates at an open end optionally having a mouthpiece 26 positioned so that a patient wearing the face mask can grip the mouthpiece with his mouth or lips and suck on the end of the Xenon gas administration tube 24. The mouthpiece may be deleted if the administration tube 24 has sufficient rigidity to prevent occlusion of the open end by a patient's lips or teeth. The other end of the administration tube 24 is connected via an interfacing means to a source 32 of Xenon gas under pressure. Preferably, the source may be a Calidose Xenon Xe 133 gas dispensing system, the Xenomatic system produced by Mallinckrodt Inc. of St. Louis, Mo., or the gas dispenser described in U.S. Pat. No. 4,192,438 to Foster et al. The interfacing means may be any conventional connection between the administration tube 24 and the source 32.

In one embodiment manually operated valve 28 may be positioned in line in Xenon gas administration tube 24 for controlling radioactive gas dispensing. A check valve 30 (FIG. 4) may also or instead be provided in order to prevent back flow of gas through the tube 24 during exhalation.

As shown in FIG. 3, bacterial/viral retentive air filter 34 may be provided in line between the breathing tube 10 and the breathing system 34. This may be a conventional disposable filter such as that manufactured by the Vital Signs Corp.

The oblique angling of the sleeve 12' in FIG. 4 permits the Xenon gas introduction system to be angled away from the patient's face, thereby reducing patient apprehension.

A particularly advantageous embodiment is illustrated in FIG. 6. There, the check valve 30 has been replaced by a Halky-Roberts type unidirectional valve 130 incorporated into a luer type port of the sleeve 12'. According to this embodiment, the sleeve 12' extends into the breathing tube 10 and includes an extension 12a, to thereby form a Y-connection. One arm of the Y shape forms an extension of the sleeve 12'. A differential pressure unidirectional valve such as a one-way duck bill valve 12b is fitted to one open end of the extension 12a (the other arm of the Y shape), while a thick walled administration tube 124, lacking a mouthpiece, is fitted to the base of the Y shape. The face mask 102 is a conventional face mask such is that produced by the Vital Signs Corporation. Corrugated tubing 104 of any desired length may be used for attaching the breathing tube 10 to the breathing system.

Figure 1:
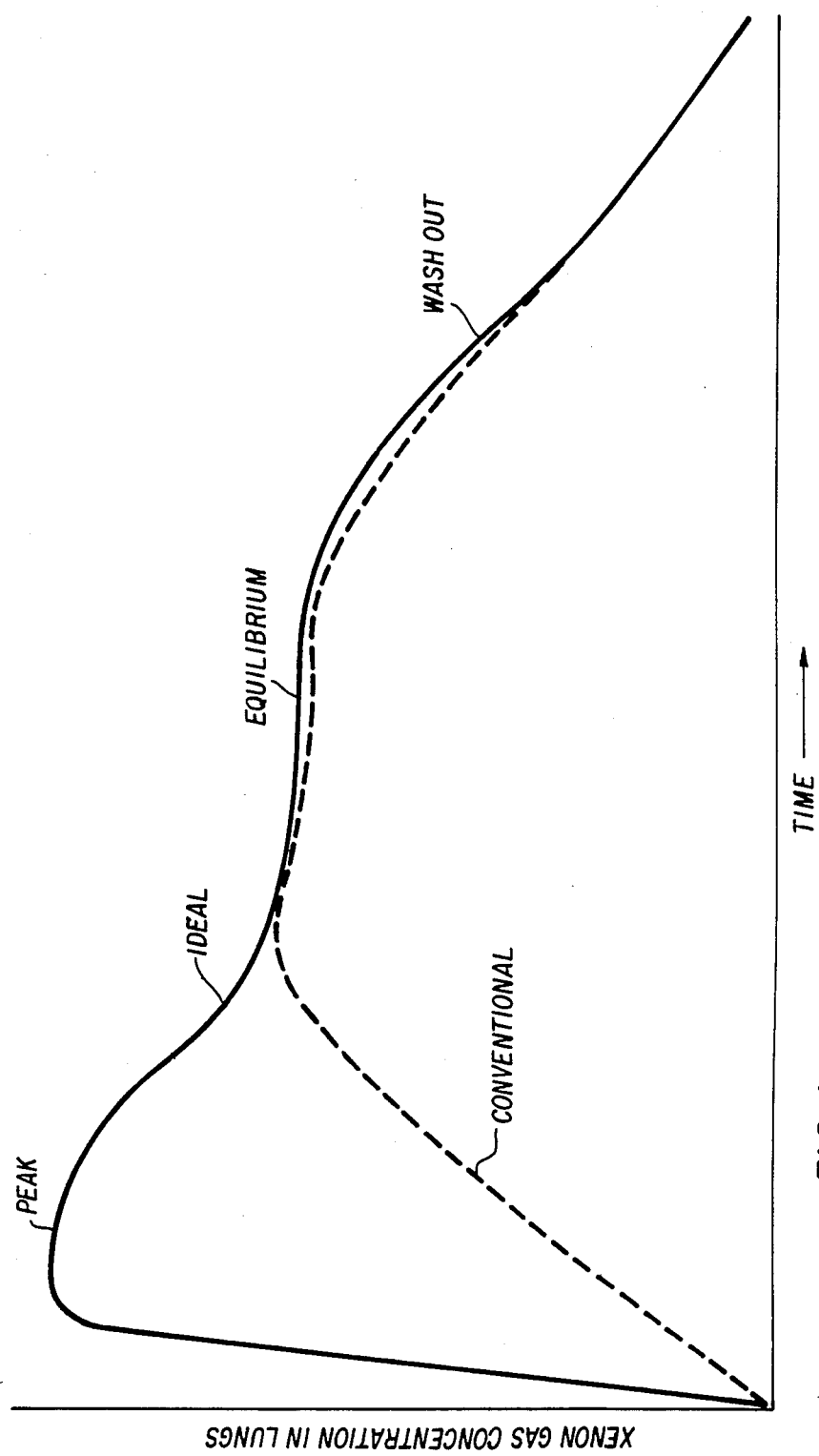
FIG. 1 is a graph illustrating Xenon gas concentration over time under both ideal and conventional conditions.

In use, the face mask is first applied to a patient's face, and the patient is permitted to breath normally while inhaling atmospheric air via the port 20 of the valve 16. Subsequently, the valve 16 is adjusted to supply purified air from the breathing system 14 via the line 18 and the patient is asked to suck on the administration tube 24. As the patient begins to suck, the Xenon gas is injected through the administration tube 24 and enters the patient's lungs as a bolus. The patient is then permitted to release the mouthpiece and breath normally into the face mask. At this time, the valve 16 is adjusted so that the exhaled breath is introduced into the breathing system 14 and purified. The use of the administration tube 24 through which the patient sucks the Xenon gas prevents dilution of the Xenon gas upon reaching the patient's lungs so that the ideal Xenon gas concentration curve of FIG. 1 can be achieved. Moreover, the use of the face mask eliminates the need for a nose clamp and substantially reduces the possibility of Xenon gas being accidently released to the atmosphere.

A potential problem with the use of the first embodiment as described above is that as the patient begins to suck on the administration tube 124 he may experience difficulty in sucking since no fluid is being delivered through the administration tube 24, and so he tends to suck out the air resident in the tube. This is avoided according to the embodiment of FIG. 6.

There, as the patient begins to suck on the administration tube 124, the sucking creates a pressure differential across the one-way valve 12b sufficient to open the one-way valve 12b. Upon the injection of the bolus of Xenon gas into the extension 124' of the administration tube 124, the pressure differential across the unidirectional valve 130 will cause the valve 130 to open and permit the Xenon gas to flow through the sleeve 12' and the administration tube 124 to the patient. The pressure differential resistance of the one-way valve 12b can be selected so that the resulting pressure increase within the sleeve extension 12a during the administration of the bolus will permit the valve 12b to momentarily close, thus avoiding the dilution of the bolus. However, as soon as the delivery of the bolus is complete, the resulting pressure drop within the administration tube extension 124' will cause the unidirectional valve 130 to close, so that continued suction by the patient will re-open the one-way valve 12b to permit air to enter the administration tube 124 behind the bolus. This provides the additional benefit that the introduction of air behind the bolus will tend to impel the bolus into the patient's airway. A further benefit of this embodiment is that the diameter of the administration tube 124 can be enlarged to further reduce the patient's breathing effort.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letter Patent of the United States is:

1. An apparatus for administering of a substance, comprising:
    a face mask defining a cavity having a face opening shaped and sized to fit over at least the mouth of a patient to define a closed space, said face mask including seal means for sealing against a face of a patient;
    conduit means for communicating said cavity with a respiratory gas volume; and
    administration means in said cavity, said administration means having an open end positionable in said face mask such that said patient wearing said face mask can suck on said open end, said administration means including interfacing means for communicating said administration means with a source of a substance.

2. The apparatus of claim 1 wherein said administration means comprises an administration tube.

3. The apparatus of claim 2, wherein said administration tube is flexible.

4. The apparatus of claim 2 including an adjustable valve in said administration means for selectively occluding said administration tube.

5. The apparatus of claim 2, wherein said open end of said administration tube has a mouthpiece.

6. The apparatus of claim 2, wherein said interfacing means further comprises means for communicating said administration tube with a source of fluid substance under pressure.

7. The apparatus of claim 1, wherein said conduit means comprises a breathing tube having an inner diameter larger than an outer diameter of said administration means, said breathing tube having one end communicating with said cavity and having another end.

8. The apparatus of claim 7 including a sealed port in said breathing tube, wherein said administration means comprises a straw-like administration tube extending from said open end thereof, into said breathing tube, through said sealed port and to said interfacing means.

9. The apparatus of claim 8, wherein said sealed port includes a sleeve angled by 90° with respect to the longitudinal axis of said breathing tube.

10. The apparatus of claim 8, wherein said sealed port includes a sleeve extending obliquely away from said face mask.

11. The apparatus of claim 8, including a filter in fluid communication with said breathing tube.

12. The apparatus of claim 8, including a differential pressure one-way valve in said breathing tube, said one-way valve comprising means for selectively permitting air in said breathing tube to enter said administration tube.

13. The apparatus of claim 12, wherein said sealed port includes a sleeve forming a Y connection in said breathing tube, the base and one arm of said Y forming a portion of said administration tube, another arm of said Y including said differential pressure one-way valve therein.

14. The apparatus of claim 13 including a unidirectional valve in said administration tube.

15. The apparatus of claim 4, wherein said face mask is non-inflatable.

16. The apparatus of claim 14, wherein said unidirectional valve forms a portion of a luer type port of said sealed port.

17. The apparatus of claim 7, wherein said breathing tube is rigid.

18. The apparatus of claim 1, including differential pressure one-way valve means forming a portion of said administration means and in fluid communication with said cavity.

19. The apparatus of claim 1, in combination with a respiratory gas volume wherein said volume is a shielded breathing system.

20. A method for administration of a substance, comprising the steps of:
 applying a face mask to the face of a patient to define a closed space;
 connecting said closed space to a shielded breathing apparatus;
 providing in said closed space an administration means having an open end positionable such that the patient can suck on said open end; and
 injecting a substance into a portion of said administration means outside of said face mask while the patient is sucking on said open end, whereby said substance is inhaled by the patient.

21. The method of claim 20, wherein said injecting step includes injecting said substance as a bolus.

22. The method of claim 21 including the step of permitting the patient to exhale said injected substance into said closed space.

23. The method of claim 22, wherein said substance is one from the group consisting of a gas, an aerosol and an insufflation.

24. The method of claim 23, wherein said substance is a radioactive gas.

25. The method of claim 24, wherein said radioactive gas is Xenon.

26. The method of claim 20 wherein said face mask is not secured to the patient by inflation of said face mask.

27. The method of claim 26 wherein the patient is human.

* * * * *